(12) United States Patent
Plank et al.

(10) Patent No.: US 7,976,307 B2
(45) Date of Patent: Jul. 12, 2011

(54) LIGHT CURING DEVICE

(75) Inventors: Wolfgang Plank, Rankweil (AT); Bruno Senn, Buchs (CH)

(73) Assignee: Ivoclar Vivadent A.G., Schaan (LI)

( * ) Notice: Subject to any disclaimer, the term of this patent is extended or adjusted under 35 U.S.C. 154(b) by 136 days.

(21) Appl. No.: 11/893,526

(22) Filed: Aug. 16, 2007

(65) Prior Publication Data

US 2008/0032254 A1 Feb. 7, 2008

Related U.S. Application Data

(60) Provisional application No. 60/880,763, filed on Jan. 17, 2007.

(30) Foreign Application Priority Data

Aug. 7, 2006 (DE) .......................... 10 2006 036 828

(51) Int. Cl.
*A61C 1/00* (2006.01)
(52) U.S. Cl. ......................................................... 433/29
(58) Field of Classification Search .................... 433/29; 250/504 H; 362/119
See application file for complete search history.

(56) References Cited

U.S. PATENT DOCUMENTS

| 4,470,101 A | * | 9/1984 | Drexler ......................... 361/802 |
| 6,890,175 B2 | * | 5/2005 | Fischer et al. .................. 433/29 |
| 6,932,599 B1 | * | 8/2005 | Hartung .......................... 433/29 |
| 7,182,597 B2 | * | 2/2007 | Gill et al. ........................ 433/29 |
| 2001/0046652 A1 | | 11/2001 | Ostler et al. |
| 2004/0053191 A1 | * | 3/2004 | Plank .............................. 433/29 |
| 2004/0185413 A1 | | 9/2004 | Gill et al. |

FOREIGN PATENT DOCUMENTS

| DE | 8135468 U | 3/1982 |
| DE | 37 19 561 A1 | 1/1988 |
| DE | 102 14 366 A1 | 10/2003 |
| DE | 10 2004 022095 A1 | 3/2005 |

* cited by examiner

*Primary Examiner* — Cris L Rodriguez
*Assistant Examiner* — Eric Rosen
(74) *Attorney, Agent, or Firm* — John C. Thompson; Alan S. Korman; Sandra J. Thompson

(57) ABSTRACT

The invention relates to a light curing device (10) having a light source (14), which is mounted such that it is thermally conductively connected to a heat sink (12), with electrical components which are fitted to a printed circuit board. The components are at least partially arranged in the cooling air stream of the heat sink (12) and the cooling air stream is at least partially guided by the printed circuit board.

18 Claims, 7 Drawing Sheets

LIGHT CURING DEVICE

CROSS-REFERENCE TO RELATED APPLICATIONS

This application claims foreign priority benefits under 35 U.S.C. §119(a)-(d) from German patent application ser. no. 10 2006 036 828.2 filed Aug. 7, 2006. In addition, this application claims the benefit under 35 U.S.C. §119(e) of U.S. provisional patent application Ser. No. 60/880,763 filed Jan. 17, 2007.

TECHNICAL FIELD

The invention relates to a light curing device, and more particularly to a light curing device which may be used in the field of dentistry wherein the light source is mounted such that it is thermally conductively connected to a heat sink, with electrical components which are fitted to a printed circuit board. The components are at least partially arranged in the cooling air stream of the heat sink and the cooling air stream is at least partially guided by the printed circuit board.

BACKGROUND OF THE INVENTION

Light curing devices in which the heat generated by the light source is dissipated using heat sinks, which are generally supplied by a fan, have been known for a long time. DE-U 81 35 468 thus exhibits a dental photopolymerization device in which a heat sink is intended to dissipate heat that is produced there. The heat sink is located in the cooling air stream of a cooling fan.

Light curing devices which operate with extremely high power have recently been disclosed. The power is generated either by LEDs or by laser diodes and is used to polymerize the dental restoration part, typically in the patient's mouth in the case of hand-held devices.

One example of such a light curing device which operates using a laser diode can be gathered from DE 37 19 561. In this solution, a heat sink having cooling ribs is fitted to the laser diode such that it is thermally conductively connected to the latter. The control electronics are held in a separate box which is protected from dust and is at a considerable distance from the heat sink.

Furthermore, DE 102 14 366 A1 by the present applicant has disclosed the practice of implementing a printed circuit to the side of a heat sink in slots which are provided between cooling ribs. This practically stops operation of the relevant cooling ribs, which is unfavorable for the relationship between cooling effect and weight.

Furthermore, the use of so-called heat pipes has also been proposed. Such heat pipes have been known for a relatively long time and are used to pass heat which has been generated at one location to a remote location and to dissipate it there. However, such solutions have proved to be rather unwieldy for light curing devices in the form of hand-held devices.

Light curing devices—especially in the form of hand-held devices—must be particularly compact. Heat sinks which are supplied with a cooling air stream, which is generated using a fan, are therefore frequently used in order to dissipate the heat generated by the light source. On the other hand, the cooling air stream must not blow out in the region of the light source, that is to say at the front of the light curing device, since otherwise the patient and the treatment site would be adversely affected by the emerging cooling air stream.

If there is a small cross section available for the cooling air stream, the fan must build up a correspondingly increased amount of pressure for the heat exchange in order to provide the desired cooling air stream for overcoming the flow resistances. It is known that a fan allows a pressure difference of at most one bar to be provided in the suction mode, this value also being able to be achieved only in theory.

Therefore, it is necessary to implement a fan in the delivery mode in order to provide a greater pressure difference.

If the direction of flow of a cooling stream in a light curing device were then desired from the front to the rear, the fan would have to be arranged, in this respect, in the front region of the light curing device if it were intended to operate in the delivery mode. On the other hand, this is not compatible with the implementation of the light source at this location.

Components which likewise have to be accommodated in the light curing device are required to electrically drive the light source. Since the heat sink-apart from the rechargeable batteries—is the heaviest component in the light curing device, it is necessary to arrange the components in a balanced manner, in which case the practice of accommodating the components in the handle of the light curing device has also already been disclosed.

OBJECTS AND SUMMARY OF THE INVENTION

Therefore, the invention is based on the object of providing a light curing device which enables a compact design without ergonomic disadvantages for a light curing device which is in the form of a hand-held device.

According to the invention, it is particularly favorable if the heat generated by the light source is immediately dissipated by the light source. To this end, it is particularly favorable, according to the invention, if a thermally conductive rod, which may have a copper core, for example, is coupled to the light source with a low thermal resistance and extends to the rear from the light source.

The thermally conductive rod then dissipates the heat of the light source to the rear, that is to say away from the patient. Cooling can then be effected using cooling ribs which are fitted to the rear end of the thermally conductive rod. This makes it possible for virtually the entire barrel of the light curing device, which is essentially in the form of a pistol, to be used for cooling. The fan can then be directly flanged to the cooling ribs on the rear part of the heat sink.

According to the invention, it is particularly advantageous if cooling is effected using a good thermal conductor which is preferably in the form of a thermally conductive metal rod. The latter is independent of position arid can reliably dissipate the heat introduced by the light source to the rear in all states. The use of a solid metal rod makes it possible to use the heat capacity of the latter, so that, as a result of the light source which is switched on, the heat capacity of the copper core is predominantly first of all used and the latter is heated up. Follower control of the fan, which is known per Se, can then be used to reliably dissipate the introduced heat in a manner distributed over time. The combination of heat dissipation very far to the rear and buffer capacity is particularly favorable since, during following, the fan does not regularly interfere since the light curing device has then already been switched off.

According to the invention, it is particularly favorable that components are at least partially arranged in the cooling air stream of the heat sink. This makes it possible, on the one hand, to save space since it is then possible to accommodate the components in a compact manner. Especially in the case of a large pressure difference generated by the fan, the additional components surprisingly do not interfere with, or virtually do not interfere with, the heat sink as the main resistance. Nevertheless, they can also be cooled in a particularly effective manner, which is particularly relevant to the operation of driving the light source especially in the case of power semiconductors.

If, for example, a multiple arrangement of light-emitting diodes is used for the light source, it is entirely possible for the power emitted to be in the region of 30 W or higher, driving expediently being effected on an unclocked basis for reasons of EMC, with the result that correspondingly high power losses of the power semiconductors arise.

The components which are situated in the cooling air stream are, as it were, automatically cooled. In addition, the printed circuit board for holding components also performs a dual function since the components are not only contact-connected and mounted there but the air flow which forms the cooling air stream is also simultaneously conducted. This ensures that the cooling air stream does not require a separate plastic insert in order to be guided, with the result that the additional weight required for this purpose can be dispensed with in a surprisingly simple manner.

In this context, it is particularly favorable that the printed circuit board can then be used practically as an additional cooling area. The copper layers which are typically implemented on the printed circuit board distribute the heat from the resistors etc., to which current has been applied, over the printed circuit board and, since the printed circuit board extends to the guide for the cooling air stream, that is to say the cooling air stream spreads along it in this respect, it is concomitantly cooled.

The invention provides for the printed circuit board to be used to guide the cooling air stream. To this end, the printed circuit board may be designed to be flat in any desired suitable manner, so that the cooling air stream spreads along one side, namely preferably that side on which said printed circuit board has been primarily fitted with components. In this context, it is preferred to implement at least two, more preferably 4, printed circuit boards which are fastened at an angle to one another so that they virtually form a type of parallelepiped in which the cooling air stream flows.

It goes without saying that, instead of this, it is also possible to implement any other desired design of the printed circuit boards and thus of the cooling air stream.

By way of example, part of the printed circuit board or an additionally small printed circuit board may also be situated in the cooling air stream in the manner of a rib, so that particularly intensive cooling is implemented there.

One advantageous refinement of the invention provides for the cooling air stream to be implemented in the blowing mode but nevertheless for the fan for generating the cooling air stream to be arranged in the rear region. This is surprisingly achieved using a flow deflection means in the front region, that is to say in the region of the light source, said deflection means being used to deflect the cooling air stream and then to supply it to lateral outlet slots which, on account of their comparatively large flow cross section, allow discharge at a low flow rate.

At the same time, the components can be arranged, according to the invention, in the cooling air stream in a particularly simple manner. To this end, they are radially arranged to the side of the thermally conductive rod and thus project into the cooling air stream behind the main cooling ribs in the direction of flow.

According to the invention, it is also favorable if at least one of the printed circuit boards is mounted on another printed circuit board such that it can be pivoted. This makes it possible, for the purposes of repair and mounting, to ensure easier access to the printed circuit board arrangement which may be in the form of a parallelepiped, for example, or else may have any other desired cross section, for example a triangular, a pentagonal or another cross section.

While four printed circuit boards are preferred for the printed circuit board arrangement, it goes without saying that, instead of this, the cooling air stream may also be guided by only two printed circuit boards, with the result that the opposite side is formed by the housing of the light curing device or an additional plastic insert.

Another advantageous refinement of the invention provides for the light curing device to have components which are situated, in particular, next to the thermally conductive metal rod on at least one printed circuit board.

Another advantageous refinement of the invention provides for at least the components to be situated at a location that is free of cooling ribs.

Another advantageous refinement of the invention provides for the components and/or the printed circuit board to be arranged such that it/they at least partially surround(s) the heat sink.

Another advantageous refinement of the invention provides for the components and/or the printed circuit board to be held in radial free spaces which are bounded by the cooling ribs of the heat sink and by a core of the heat sink.

Another advantageous refinement of the invention provides for at least one printed circuit board to be at least partially mounted on the heat sink and to extend, in particular, along the side of the heat sink.

Another advantageous refinement of the invention provides for at least three printed circuit boards, in particular four printed circuit boards, to surround the heat sink.

Another advantageous refinement of the invention provides for at least one printed circuit board to be mounted such that it can be moved, in particular pivoted, relative to another printed circuit board.

Another advantageous refinement of the invention provides for the printed circuit board to be fitted, in particular, with all of the components on its side that faces the heat sink or on its side that is remote from the heat sink.

Another advantageous refinement of the invention provides for at least one printed circuit board to be applied to the thermally conductive metal rod of the heat sink and to rest there in an insulated manner and to be, in particular, thermally conductively connected to the thermally conductive rod.

Another advantageous refinement of the invention provides for the thermally conductive metal rod to be essentially in the form of a parallelepiped and to be surrounded on all four sides, in particular, by printed circuit boards.

Another advantageous refinement of the invention provides for the components to be thermally conductively connected to the printed circuit board and for the printed circuit board to be in the form of a cooling element which can be used to dissipate the heat, which is emitted by the components and is introduced into the printed circuit board, via the cooling air stream.

Another advantageous refinement of the invention provides for a first cooling air duct to extend between at least one printed circuit board and the thermally conductive rod and/or heat sink.

Another advantageous refinement of the invention provides for a second cooling air duct to extend between the printed circuit boards and a housing of the light curing device or between two housing parts of the light curing device.

Another advantageous refinement of the invention provides for a deflection means for the cooling air stream to be provided adjacent to the light source between two S housing parts or between at least one printed circuit board and the housing, which deflection means is used to deflect the cooling air stream by at least 90°, in particular by more than 150°.

Another advantageous refinement of the invention provides for the cooling air stream to be generated by a fan and for the cold air to be applied to the cooling ribs and, in particular, also to the components.

Another advantageous refinement of the invention provides for the fan to be arranged at that end of the heat sink which is remote from the light source.

Another advantageous refinement of the invention provides for the cooling air stream to first of all pass through the first cooling air duct and, after being deflected, to pass through the second cooling air duct or vice versa.

Another advantageous refinement of the invention provides for the cooling air stream, after it has passed through the two cooling air ducts, to leave the housing in an end region of a handle of the light curing device.

Another advantageous refinement of the invention provides for two mutually opposite printed circuit boards to project toward the light source and to make contact there with connection lugs of an end printed circuit board which essentially extends at right angles to the printed circuit boards and which is used to connect the light source.

Another advantageous refinement of the invention provides for the thermally conductive rod to comprise copper, in particular, and for the heat sink to comprise aluminum or an aluminum alloy, in particular.

Another advantageous refinement of the invention provides for the components, when seen over the longitudinal extent of the heat sink, to be arranged at the level of the thermally conductive rod with a low thermal resistance or a heat pipe.

BRIEF DESCRIPTION OF THE FIGURES

Further advantages, details and features emerge from the following description of two exemplary embodiments of the invention with reference to the drawing, in which.

DETAILED DESCRIPTION

Figure 1:
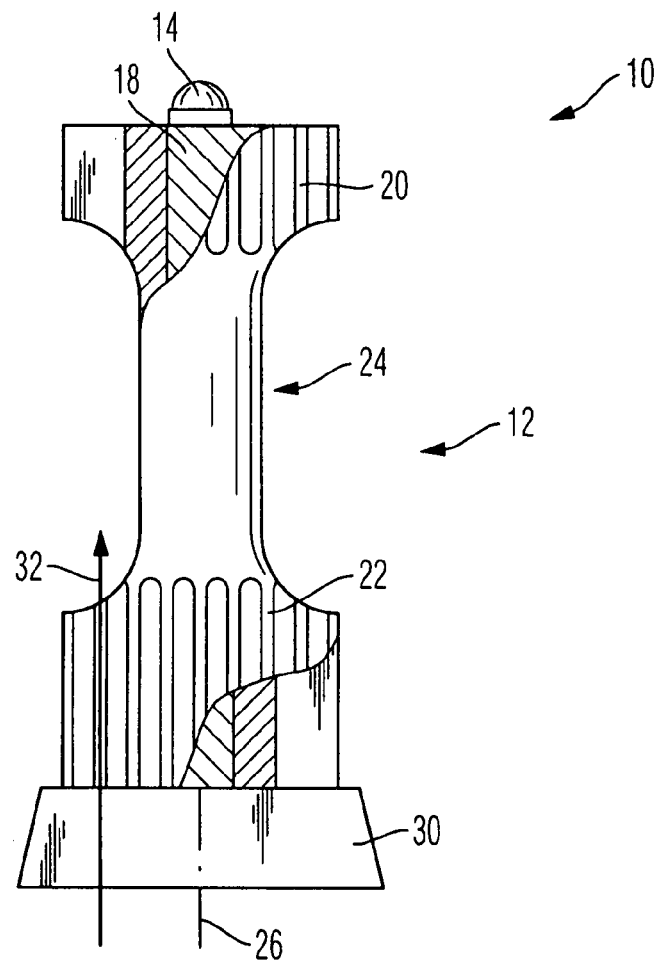
FIG. 1 shows a side view of part of a light curing device according to the invention, with the heat sink, inter alia, being illustrated.

The light curing device 10, part of which is illustrated in FIG. 1, has a heat sink 12 which is arranged in the barrel of the light curing device which is in the form of a pistol. In a manner known per Se, a set of rechargeable batteries and an initiation button are fitted in the handle of the light curing device, and a display device for displaying the operating state of the light curing device, which is in the form of a hand-held device, is additionally fitted on the top side.

The heat sink 12 is fitted with a light source 14 at its front end. The light source 14 may be in the form, for example, of an LED or a multiple arrangement of LEDs and emits both light and heat. The optical power emitted is passed, via an optical waveguide—if necessary with the aid of reflectors—into the patient's mouth when the dentist is light-curing the dental restoration part.

The light source is directly or indirectly connected to a good thermal conductor, in particular a thermally conductive metal rod, whose end region, which is remote from the light source, is at least thermally conductively connected to cooling ribs 20, 22 of the heat sink. The light source is thermally conductively connected to the heat sink 12 in an effective manner. The heat sink 12 has, as a copper core, a thermally conductive rod 18 which extends centrally, so that the heat is dissipated in the axial direction of the elongate heat sink 12 in a particularly effective manner. The heat sink is comprised of aluminum or an aluminum alloy.

The heat sink 12 has an essentially dumbbell-like design. Cooling ribs 20 extend in the form of a star in the front region of said heat sink, that is to say that region which is adjacent to the light source 14. In addition, cooling ribs 22 likewise extend in the form of a star in the rear region of said heat sink, while a recess 24 which extends in a circular manner and provides a free space is provided between the front and rear cooling ribs 20 and 22.

All of the cooling ribs 20 and 22 extend parallel to an axis 26 of the heat sink 12 that coincides with the optical axis of the light source 14. The cooling ribs 22 are considerably longer than the cooling ribs 20 in the axial direction. While each cooling rib 20 is approximately as long as it is high, the cooling ribs 22 take up approximately one third of the overall length of the heat sink 12.

A fan 30 which passes a cooling air stream 32 through the heat sink 12 is flanged to the rear end of the heat sink 12 which is essentially parallelepipedal in cross section or else, in a modified refinement, circular in cross section. The cooling air stream spreads along the cooling ribs 20 and 22 and also passes through the recess 24. It is in the form of a compressed air stream, as is explained in detail further below.

Figures 2, 3:
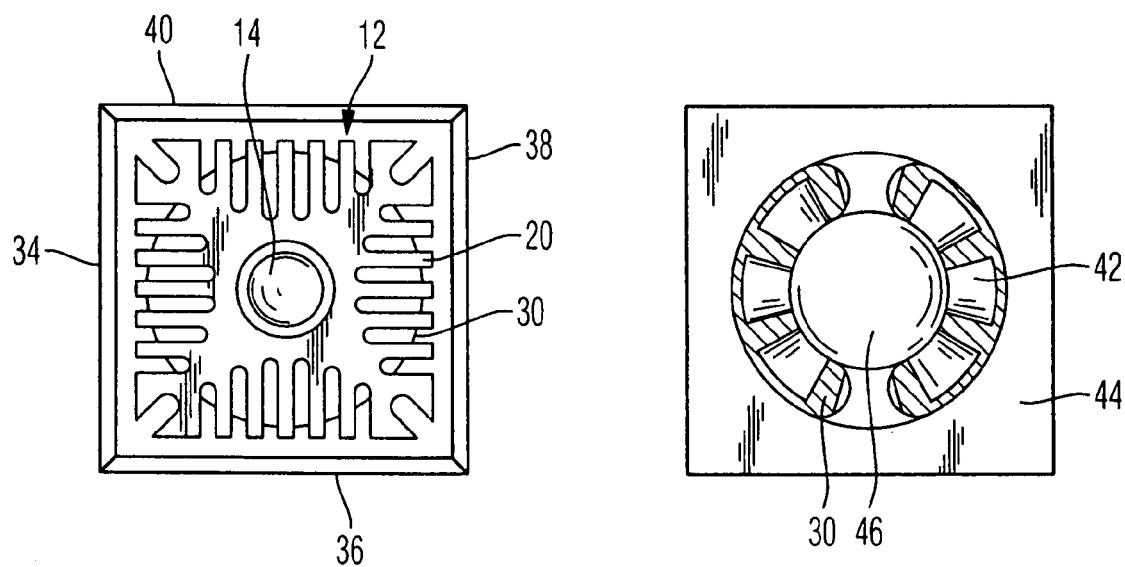
FIG. 2 shows an end view of the embodiment according to FIG. 1 from the front.
FIG. 3 shows a rear view of the embodiment according to FIG. 2.

FIG. 2 shows how the heat sink 12 can be configured. In this case, and in the further figures, the same reference symbols refer to identical or corresponding parts.

In the front region, the heat sink 12 has the cooling ribs 20 which can be seen in FIG. 2. The fan 30 with its flow outlet can be seen through the longitudinally extending cooling ribs 20 and 22.

The light curing device has printed circuit boards 34, 36, 38 and 40 which surround the heat sink 12 and, in this respect, extend essentially in the form of a parallelepiped. The printed circuit boards completely surround the heat sink 12 and, in this respect, form a flow duct for the purpose of providing the cooling air stream through the heat sink. At least one of the printed circuit board is at least partially mounted on the heat sink and along the side of the heat sink. While four printed circuit boards are illustrated in FIG. 2, it should be understood that the heat sink could have differing configurations, for example triangular in cross section, in which case only there circuit boards would be employed. Other cross-sectional configurations are also possible, leading to differing numbers of printed circuit boards.

FIG. 3 shows the design of the fan 30. The fan 30 has two mutually opposite air inlet slots 42 which are left in a rear wall 44 of the fan housing. In a manner known per se, the fan 30 is driven using an electric motor 46.

Figure 4:
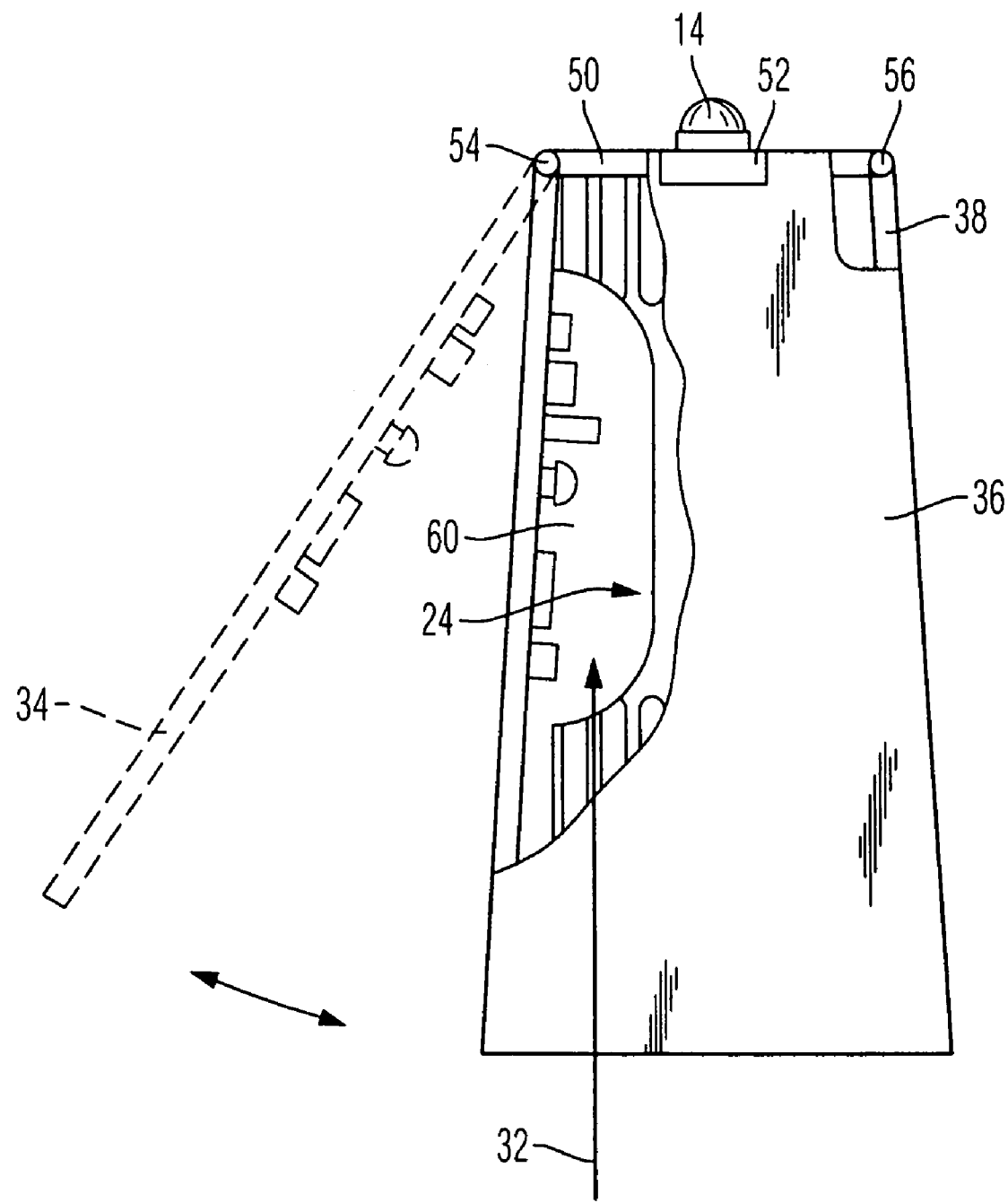
FIG. 4 shows a view of the embodiment according to FIGS. 1 to 3, at least two printed circuit boards having already been mounted.

FIG. 4 shows how the structure comprising the heat sink and printed circuit boards can be assembled. A front printed circuit board 50 surrounds the light source 14 which is connected to the thermally conductive rod 18 (not illustrated) via a substrate 52. The circuit board or boards rest on the thermally conductive metal rod in an insulated manner and is thermally conductively connected to the thermally conductive rod. The printed circuit boards which essentially extend in an axially parallel manner are connected in an articulated manner via the printed circuit board 50. To this end, a respective joint is provided, the joints 54 and 56 being illustrated by way of example in FIG. 4. The printed circuit board 34 is illustrated in the pivoted-out state, while the printed circuit boards 36 and 38 are illustrated in the fully assembled state.

The printed circuit boards are each fitted with components, a multiplicity of components 60 being illustrated by way of example for the printed circuit board 34. The components are thermally conductively connected to the printed circuit board, and the circuit board is in the form of a cooling element which can be used to dissipate the heat which is emitted by the components. The components 60 extend into the recess 24 and, in this respect, are situated in the cooling air stream 32 of the fan 30. In addition, they are thermally conductively connected in an effective manner to the printed circuit board 34, along which cooling air likewise spreads over a large area. As a result of this and as a result of the copper conductors provided on the printed circuit board 34, the components 60 are likewise cooled effectively. The components 60 can be situated next to the thermally conductive metal rod on at least one printed circuit board and can be in a location free of cooling ribs. The components and/or the printed circuit board 34, 36, 38, 40 can be arranged so that they at least partially surround the heat sink 12. The components and/or the printed circuit board are held in radial free spaces which are bounded by the cooling ribs of the heat sink and by a core of the heat sink.

The printed circuit boards 34 to 40 do not extend exactly in the form of a parallelepiped but rather taper slightly to the front. As a result of this, the flow cross section is larger in the region of the rear cooling ribs 22 and smaller in the region of the front cooling ribs 20. The flow rate is correspondingly higher in the front hot region, while more time remains for the cooling air to absorb the heat in the rear region.

Figure 5:
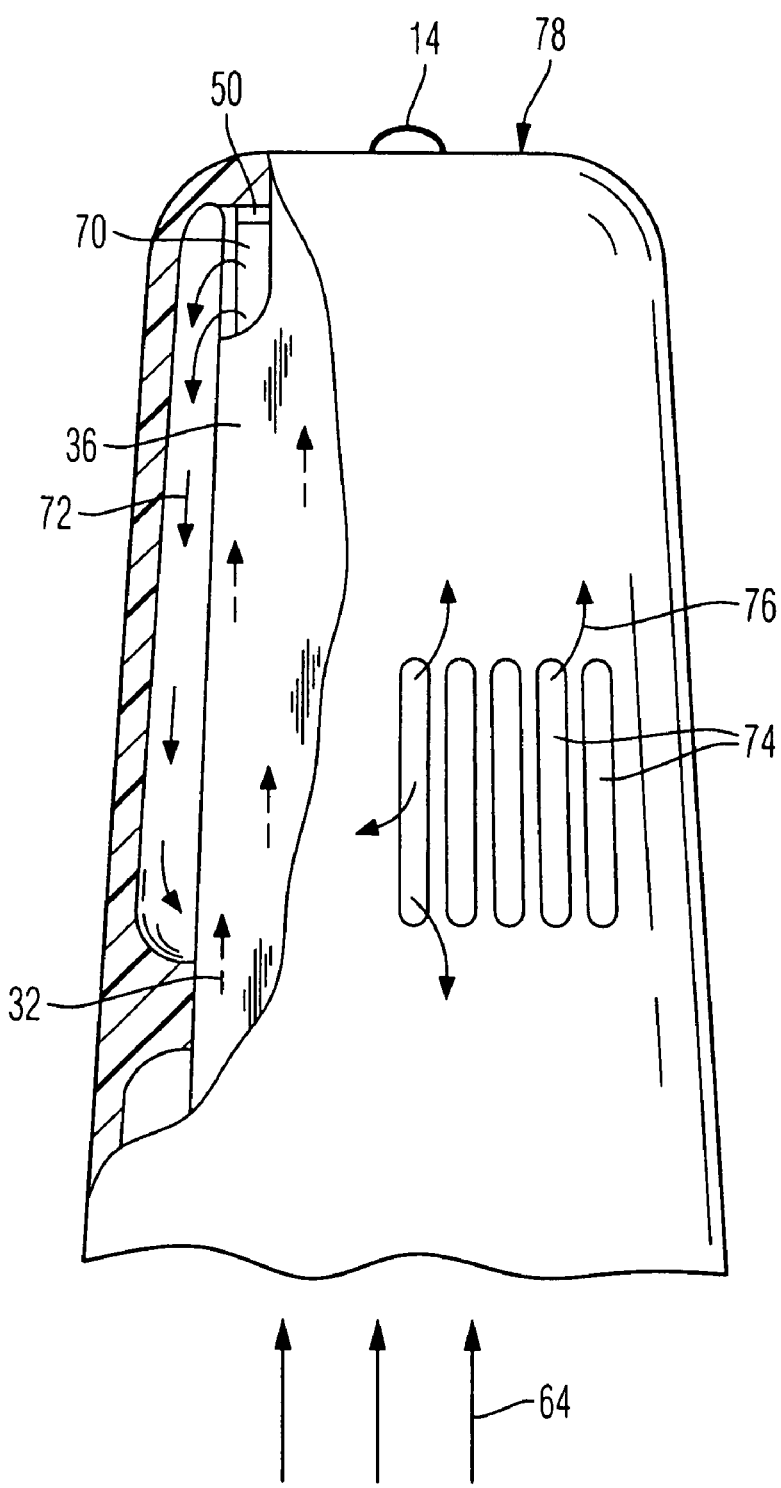
FIG. 5 shows a side view of the light curing device according to the invention in a more assembled state.

FIG. 5 shows how the cooling air stream 32 is deflected. The cooling air is first of all introduced into the heat sink via the fan in accordance with the arrows 64 and flows to the front, that is to say in the direction of the light source 14. A deflection means 70 for the cooling air stream is provided in the front corners of the printed circuit board arrangement which is essentially in the form of a parallelepiped. The deflection means is located adjacent to the light source between two housing parts or between at least one printed circuit board and the housing, and is used to deflect the cooling air stream 32 by at least 90 degrees, and in particularly by more than 150 degrees. The printed circuit board arrangement correspondingly has, in practice, relatively large and broad slots in the front corners, said slots making it possible to deflect the cooling air stream to the rear. The cooling air stream thus extends to the rear in accordance with the arrows 72.

Cooling air slots 74 which extend outward and make it possible for the used cooling air to emerge over a large area in accordance with the arrows 76 are formed approximately in the axial center of the heat sink. This guidance of the cooling air makes it possible to supply the cooling air stream 32 in the form of compressed air, the front region 78 of the light curing device nevertheless remaining completely free of cooling air and, in particular, cooling air not being blown onto the patient.

Figure 6:
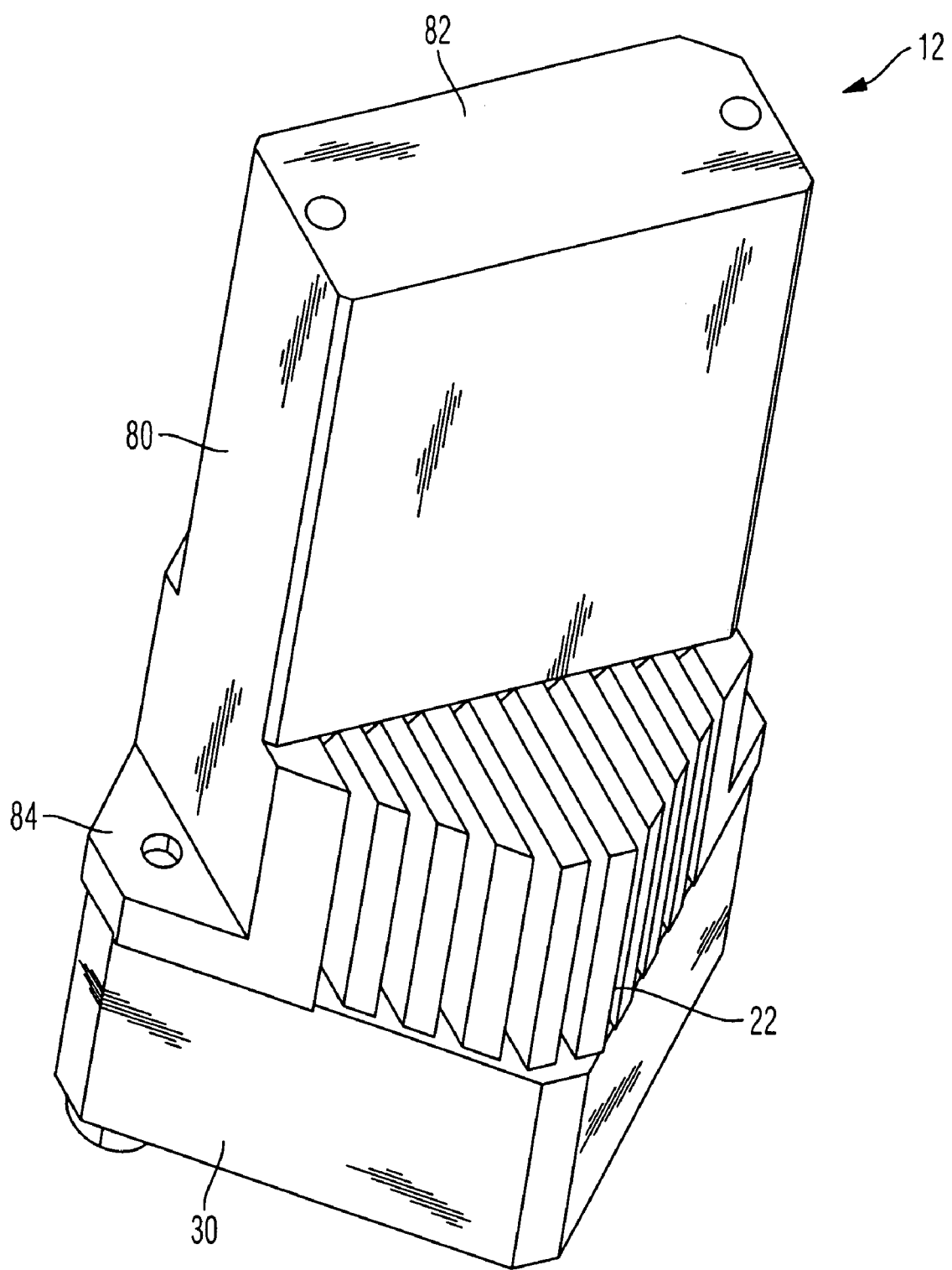
FIG. 6 shows a perspective view of a heat sink without printed circuit boards in another embodiment but with a fan that has been mounted.
Figure 7:
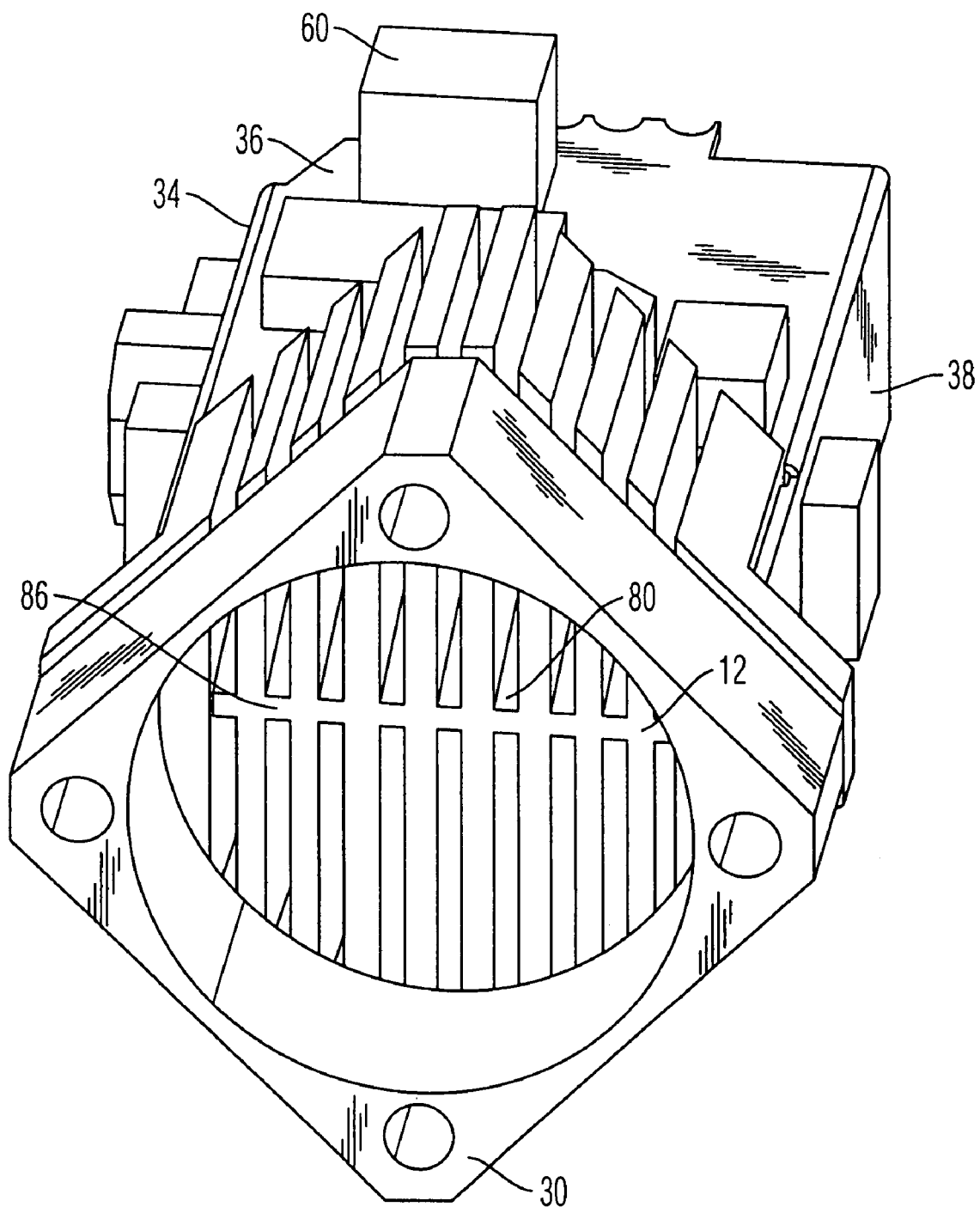
FIG. 7 shows a rear view of the heat sink according to FIG. 6, printed circuit boards and components having been mounted.
Figure 8:
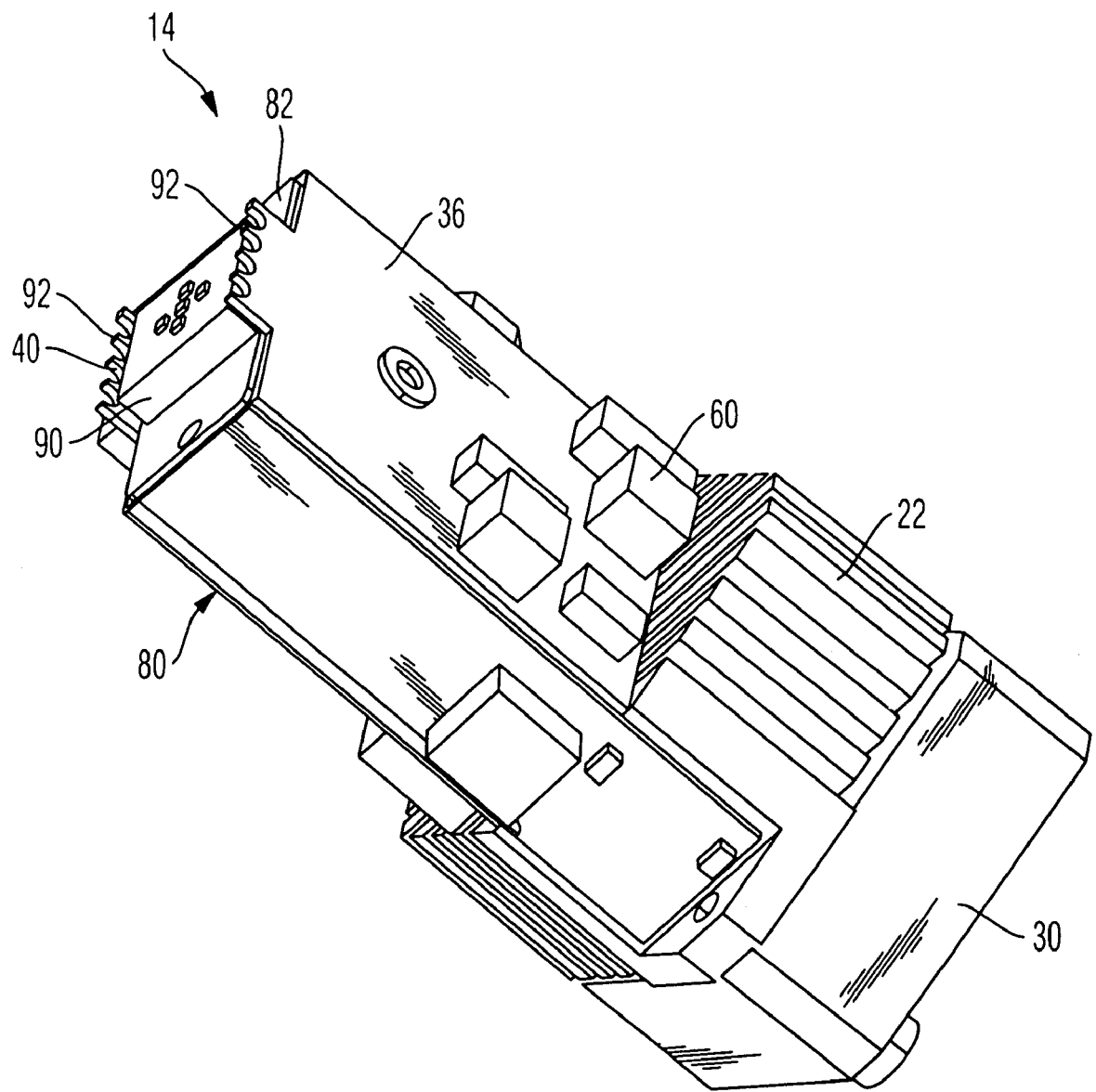
FIG. 8 shows the assembled unit comprising the heat sink, fan and printed circuit boards including the components and the light source.

FIGS. 6 to 8 show another embodiment. In this embodiment, the heat sink 12 has a thermally conductive rod 80 which essentially extends in the longitudinal direction in the form of a parallelepiped, comprises solid highly thermally conductive metal and is intended to hold the light source on its front end face 82. The thermally conductive metal rod is surrounded on all four sides by printed circuit boards 34, 36, 38, 40.

In this embodiment, an additional cooling rib arrangement is not provided adjacent to the light source. For this purpose, the thermally conductive rod 80 has a copper core which cannot be seen in FIG. 6 and has, in its rear region, the cooling ribs 22 which, in this respect, are connected to the light source with an extremely low thermal resistance.

Flanged to the cooling ribs is the fan 30 whose outer circumference essentially corresponds to the extent of the cooling ribs, thus producing a compact unit comprising the heat sink 12 and the fan 30. It is particularly favorable that the essentially square housing of the fan 30 is arranged such that it is offset at an angle of approximately 45° with respect to the transverse extent of the thermally conductive rod 80, so that the fan 30 can be effectively fastened via a flange 84 and the cooling ribs 22 nevertheless extend over virtually the entire effective area of the fan 30.

As can be seen in FIG. 7, provision is made, for this purpose, for the thickness of the thermally conductive rod 80 to decrease in the transverse direction toward the fan 30. Following the fan 30, the thermally conductive rod 80 is tapered, in this respect, to a narrow web 86 whose width corresponds approximately to the width of a cooling rib. This also produces a comparatively low flow resistance for the fan 30 which is in the form of a radial fan.

As can also be seen in FIG. 7, provision is made for printed circuit boards (of which the printed circuit boards 34, 36 and 38 can be seen in FIG. 7) to surround the thermally conductive rod 80 over a large area, the components 60 extending, in this embodiment, on that side of the printed circuit boards 34 to 38 which is remote from the heat sink. This allows an extensive thermally conductive connection between the printed circuit boards 34 to 38 and the thermally conductive rod 80, so that solid cooling can be implemented for the components 60. In this embodiment as well, the components 60 are additionally located in the cooling air stream and it is preferred for those components 60 which are particularly sensitive to heat to be arranged on the printed circuit board 36 and the printed circuit board 40, which are located fully in the cooling air stream, while the cooling air stream for the components on the printed circuit boards 34 and 38 is provided merely as a secondary air stream. Alternatively, the components can be fitted on the side of the circuit board that is remote from the heat sink.

FIG. 8 shows how the light source 14 can be applied to the end face 82 of the thermally conductive rod 80. In this embodiment, the light source 14 has five LED chips which are arranged in the form of a cross and are applied to a common substrate 90 which is in contact with the end face 82 over a large area, so that the heat generated by the light source 14 is introduced into the thermally conductive rod 80 with a very low thermal resistance.

In this embodiment, the printed circuit boards 36 and 40 are pulled to the front over the substrate 90, with the result that they provide connection lugs 92 which are available for making contact with the end printed circuit board (not illustrated)

on the substrate 90 for the purpose of supplying the light source. The end printed circuit board then extends between the connection lugs 92 of the mutually opposite printed circuit boards 36 and 40 at essentially right angles to the printed circuit boards, and is used to connect the light source.

Since broad copper tracks are used to implement a low electrical resistance in this case, the heat which is introduced is additionally also passed, via these conductor tracks, into the rear region, where cooling for the printed circuit boards 36 and 40 is effected extensively by means of the intensive cooling air stream which is generated by the fan 30.

Figure 9:
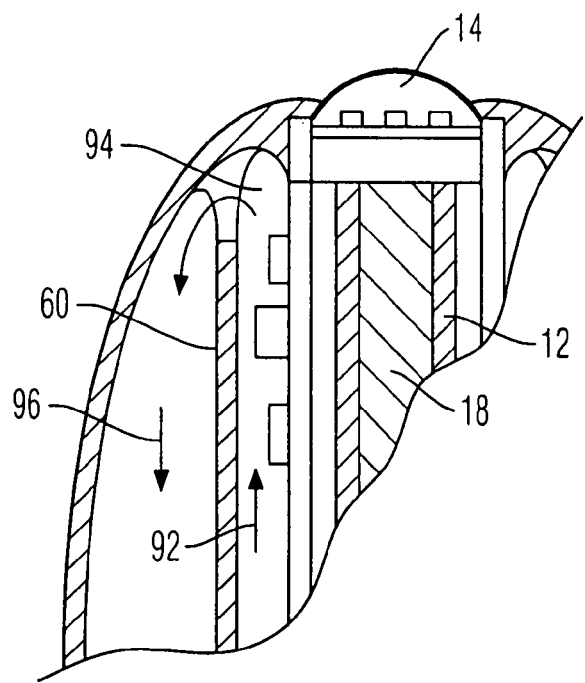
FIG. 9 shows a partially broken-away illustration of a detail of a light curing device according to the invention.
Figure 10:
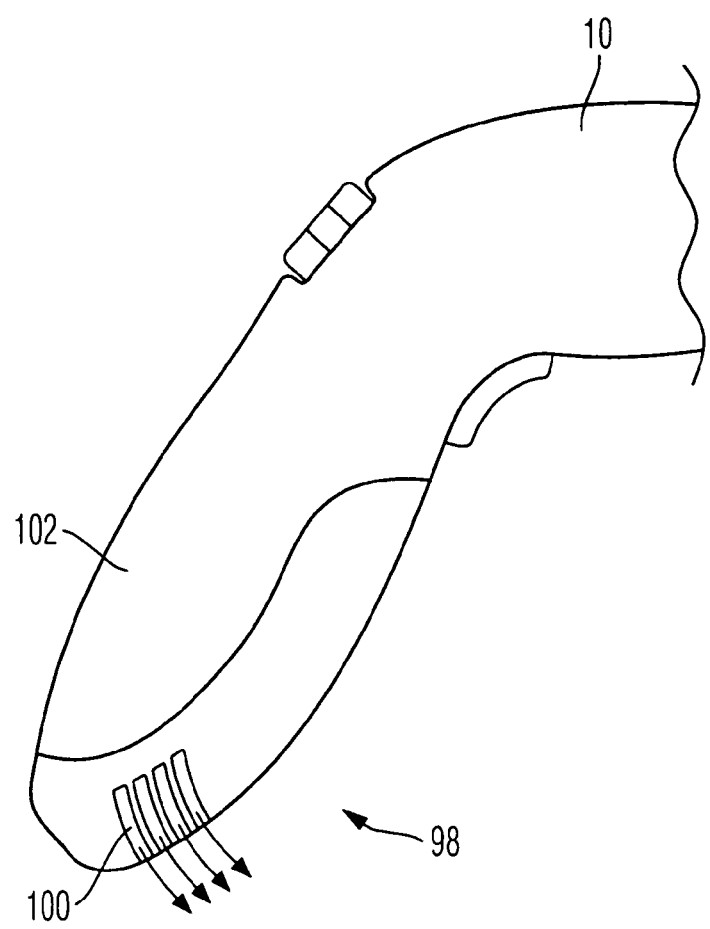
FIG. 10 shows a side view of the light curing device according to the above FIGures.

FIG. 9 shows that the cooling air stream is preferably deflected in order to achieve the desired cooling, in particular of the components 60 as well. After passing through the first cooling air duct 92 in the region of the components, the cooling air stream is deflected in the region of a deflection means 94, which is adjacent to the light source 14, to a second cooling air duct 96, which extends between the printed circuit boards and a housing of the light curing device or between two housing parts. The air flows along the inside of the housing there and emerges—as can be seen in FIG. 10—from a handle 102 of the light curing device 10 which is in the form of a pistol at cooling air slots 100 at the rear end 98. Alternatively, the air flow can pass through the second cooling air duct and then through the first cooling air duct.

While a preferred form of this invention has been described above and shown in the accompanying drawings, it should be understood that applicant does not intend to be limited to the particular details described above and illustrated in the accompanying drawings, but intends to be limited only to the scope of the invention as defined by the following claims. In this regard, the term "means for" as used in the claims is intended to include not only the designs illustrated in the drawings of this application and the equivalent designs discussed in the text, but it is also intended to cover other equivalents now known to those skilled in the art, or those equivalents which may become known to those skilled in the art in the future.

What is claimed is:

1. A light curing device having a light source, wherein the light source is connected to a good thermal conductor (18) which extends into a heat sink (12) provided with a front end portion adjacent to the light source, a rear end portion, and an intermediate portion formed therebetween, with cooling ribs (20) of the front end portion of the heat sink extending radially beyond the intermediate portion and with cooling ribs (22) of the rear portion extending radially beyond the intermediate portion, wherein the light curing device has components (60) which are placed on at least one printed circuit board (34, 36, 38, 40) which protrudes into the intermediate portion of the heat sink, wherein the rear portion has a first diameter, the front end portion has a second diameter, the intermediate portion has a third diameter, wherein the third diameter is less than both the first and second diameters; wherein the cooling ribs of the front end portion extend from the end of the heat sink adjacent the light source towards the rear portion and terminate at the intermediate portion, wherein the cooling ribs of the rear portion extend from an end opposite the light source towards the front end portion and terminate at the intermediate portion, and wherein there are no cooling ribs located in the intermediate portion.

2. The light curing device as claimed in claim 1, wherein at least the components (60) are situated at a location that is free of cooling ribs.

3. The light curing device as claimed in claim 1, wherein the components (60) and/or printed circuit board (34, 36, 38, 40) is/are arranged such that it/they at least partially surround(s) the heat sink (12).

4. The light curing device as claimed in claim 1, wherein the components (60) and/or printed circuit board is/are held in radial free spaces which are bounded by the cooling ribs (20, 22) of the heat sink (12) and by a core of the heat sink (12).

5. The light curing device as claimed in claim 1, wherein at least one printed circuit board is at least partially mounted on the heat sink (12) and extends along the side of the heat sink (12).

6. The light curing device as claimed in claim 1, wherein at least three printed circuit boards (34, 36, 38, 400 surround the heat sink (12).

7. The light curing device as claimed in claim 1, wherein at least one printed circuit board is mounted such that it can be moved relative to another printed circuit board.

8. The light curing device as claimed in claim 1, wherein a printed circuit board is fitted with all of the components (60) on either its side that faces the heat sink (12) or on its side that is remote from the heat sink (12).

9. The light curing device as claimed in claim 1, wherein the heat sink is a thermally conductive rod, and wherein at least one printed circuit board (34, 36, 38, 40) is applied to the thermally conductive metal rod of the heat sink (12) and rests there in an insulated manner and is thermally conductively connected to the thermally conductive rod.

10. The light curing device as claimed in claim 9, wherein the thermally conductive metal rod is essentially in the form of a parallelepiped and is surrounded on all four sides by four printed circuit boards (34, 36, 38, 40).

11. The light curing device as claimed in claim 1, wherein the components (60) are thermally conductively connected to a printed circuit board and the printed circuit board is in the form of a cooling element which can be used to dissipate the heat, which is emitted by the components (60) and is introduced into the printed circuit board, via a cooling air stream (32).

12. The light curing device as claimed in claim 1, wherein a first cooling air duct extends between at least one printed circuit board (34, 36, 38, 40) and the heat sink (12).

13. The light curing device as claimed in claim 12, wherein a second cooling air duct extends between the at least one printed circuit board and a housing of the light curing device or between two housing parts of the light curing device.

14. The light curing device as claimed in claim 13, wherein a deflection means for the cooling air stream (32) is provided adjacent to the light source between two housing parts or between at least one printed circuit board and the housing, which deflection means is used to deflect the cooling air stream (32) by at least 90 degrees.

15. The light curing device as claimed in claim 13, wherein a cooling air stream first of all passes through the first cooling air duct and, after being deflected, passes through the second cooling air duct or vice versa.

16. The light curing device as claimed in claim 15, wherein the cooling air stream, after it has passed through the two cooling air ducts, leaves the housing in an end region of a handle of the light curing device.

17. The light curing device as claimed in claim 1, wherein a cooling air stream from a fan is applied to the cooling ribs (20, 22) and also to the components (60).

18. The light curing device as claimed in claim 17, wherein the fan is arranged at that end of the heat sink (12) which is remote from the light source.

* * * * *